(12) United States Patent
Fricker et al.

(10) Patent No.: US 8,353,941 B2
(45) Date of Patent: Jan. 15, 2013

(54) SLEEVE

(75) Inventors: Renato Fricker, Basel (CH); Hans Gelpke, Wiesendangen (CH); Romano Matthys, Davos Clavadel (CH)

(73) Assignee: Synthes USA, LLC, West Chester, PA (US)

( * ) Notice: Subject to any disclaimer, the term of this patent is extended or adjusted under 35 U.S.C. 154(b) by 1103 days.

(21) Appl. No.: 11/569,953

(22) PCT Filed: Jun. 2, 2004

(86) PCT No.: PCT/CH2004/000330
§ 371 (c)(1),
(2), (4) Date: Feb. 4, 2008

(87) PCT Pub. No.: WO2005/117727
PCT Pub. Date: Dec. 15, 2005

(65) Prior Publication Data
US 2008/0255621 A1 Oct. 16, 2008

(51) Int. Cl.
*A61B 17/04* (2006.01)
(52) U.S. Cl. .................................... 606/302
(58) Field of Classification Search .......... 606/300–331, 606/104, 103; 411/378–426
See application file for complete search history.

(56) References Cited

U.S. PATENT DOCUMENTS

| | | | |
|---|---|---|---|
| 3,506,411 A | 4/1970 | Robins | |
| 4,836,196 A * | 6/1989 | Park et al. | 606/246 |
| 5,217,462 A * | 6/1993 | Asnis et al. | 606/916 |
| 5,643,274 A * | 7/1997 | Sander et al. | 606/104 |
| 5,649,963 A * | 7/1997 | McDevitt | 606/232 |
| 6,039,738 A * | 3/2000 | Sanders et al. | 606/86 A |
| 6,179,841 B1 * | 1/2001 | Jackson | 606/301 |
| 6,287,311 B1 * | 9/2001 | Sherman et al. | 606/78 |
| 6,858,031 B2 * | 2/2005 | Morrison et al. | 606/292 |
| 7,044,953 B2 * | 5/2006 | Capanni | 606/309 |
| 7,789,896 B2 * | 9/2010 | Jackson | 606/266 |
| 7,846,167 B2 * | 12/2010 | Garcia et al. | 606/104 |
| 7,914,558 B2 * | 3/2011 | Landry et al. | 606/246 |
| 2002/0072750 A1 * | 6/2002 | Jackson | 606/73 |
| 2003/0199873 A1 * | 10/2003 | Richelsoph | 606/61 |
| 2004/0097953 A1 * | 5/2004 | Krenkel et al. | 606/105 |
| 2004/0133207 A1 * | 7/2004 | Abdou | 606/73 |

(Continued)

FOREIGN PATENT DOCUMENTS

DE 1 615 657 7/1970

(Continued)

OTHER PUBLICATIONS

International Search Report of PCT/CH2004/000330.

*Primary Examiner* — Kevin T Truong
*Assistant Examiner* — Christopher Beccia
(74) *Attorney, Agent, or Firm* — Fay Kaplun & Marcin, LLP

(57) ABSTRACT

The invention relates to a sleeve (1), for a bone fixation element, in particular, a wire (10), comprising A) two tubular elements (3; 4), having a common longitudinal axis (2), each with a central drilling (8) of the same diameter (D), an external end (20; 21) and an intermediate end (22; 23) with a front face (28; 29) and B) a shearable connector web (5), fixed to the two tubular elements (3; 4), outside the central drilling (8), by means of which the two tubular elements (3; 4) are axially connected to each other.

20 Claims, 3 Drawing Sheets

U.S. PATENT DOCUMENTS

2008/0140120 A1 * 6/2008 Hestad et al. ................ 606/246

FOREIGN PATENT DOCUMENTS

| | | |
|---|---|---|
| DE | 29 34 094 | 3/1981 |
| EP | 0 452 086 A1 | 10/1991 |
| EP | 0 634 536 A1 | 1/1995 |
| FR | 2 333 149 | 6/1977 |
| FR | 2 611 241 | 8/1988 |
| NL | 7 012 094 | 2/1972 |

* cited by examiner

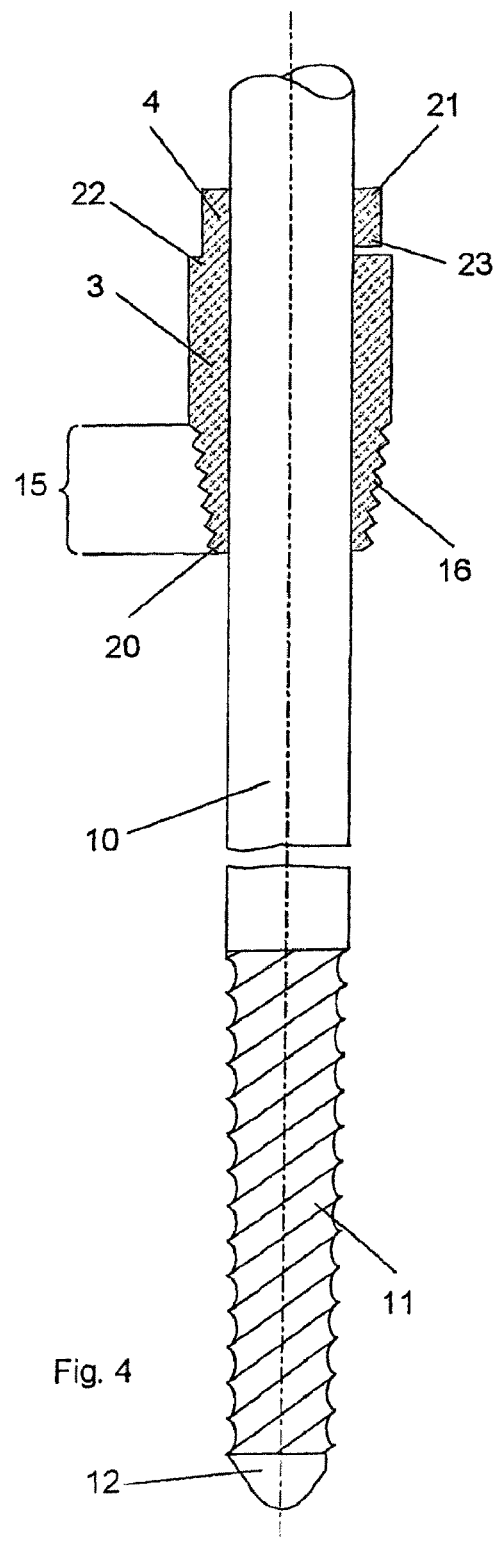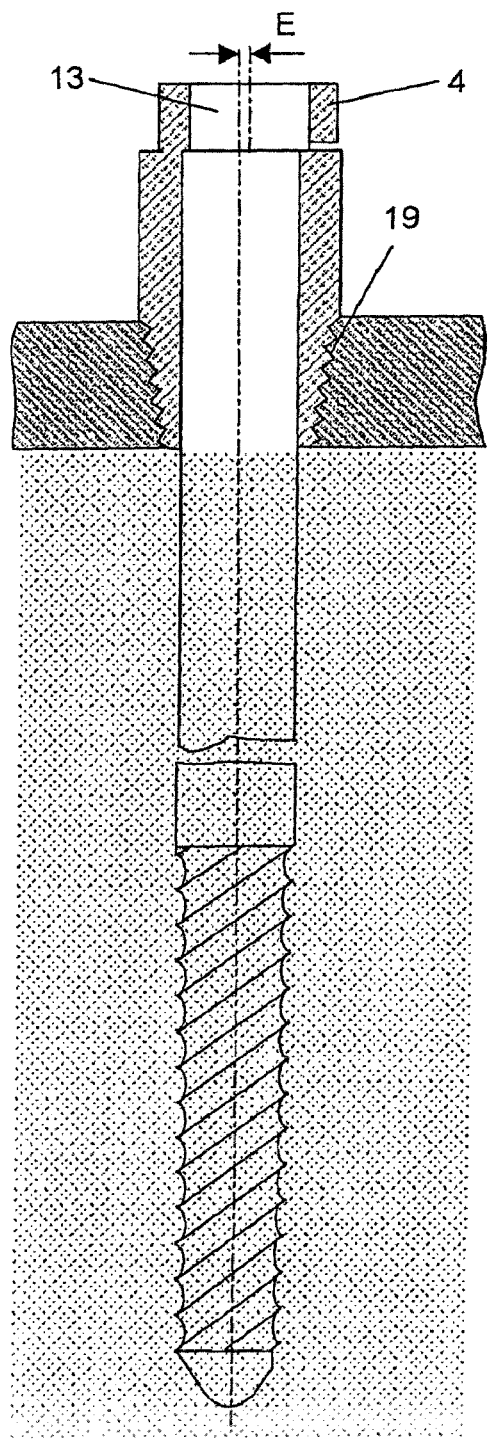

SLEEVE

RELATED APPLICATION DATA

This application is the U.S. National State application of International Application No. PCT/CH2004/000330, filed Jun. 2, 2004.

FIELD OF THE INVENTION

The invention relates to a sleeve which is mountable as the end protection or head on a longitudinal bone fixation element, in particular a cylindrical or hollow cylindrical wire, according to the preamble of Patent claim 1 and it relates to a device for fixation of bones or bone fragments according to the preamble of claim 15.

BACKGROUND OF THE INVENTION

Kirschner wires, pins or Schanz screws are often used in surgery and for a wide variety of applications. Such thin wires or screws are first attached to a bone or bone fragment at their distal end and then attached to an external fixator in accordance with their function. After being attached to the bone, wires are cut to their desired length.
Disadvantages of this technique include the fact that
   after being cut, the free end of the wire has a burr which may cause irritation to the adjacent soft tissue; and
   use of such wires is limited by the fact that practically only force-locking connections to other parts, e.g., screw heads or other anchoring elements, may be used on the proximal end of the wire. However this is unfavorable for applications as compression screws.

DE 94 90 219 to HOWMEDICA discloses, for example, a compression device comprising a longitudinal bone fixation element with an axially displaceable stopper that can be locked in the desired position. The shaft and the central bore in the stopper each have a non-round cross-sectional area, so that the stopper is also locked with regard to rotation about the longitudinal axis of the bone fixation element. One disadvantage of this known device is that the bone fixation element must be designed like a toothed rack, which means a complex manufacturing process and thus high costs.

SUMMARY OF THE INVENTION

The present invention seeks to remedy this situation. The invention is based on the object of creating a sleeve which has an aligned central bore in the undeformed state and is deformable by shearing across its longitudinal axis without applying any great force, such that it has two axial segments that are joined together and have central bores that are not aligned.

The present invention achieves the object as formulated with a sleeve having the features of claim 1 and a device for fixation of bones or bone fragments having the features of claim 15.

Additional advantageous embodiments of the invention are characterized in the dependent claims.

The advantages achieved through the invention can essentially be regarded as the fact that, thanks to the inventive sleeve,
   the end of a severed wire can be designed to be free of any burr by applying a sleeve. The edge formed by the severing operation on the wire is covered by the sleeve; and
   sleeve can be attached in a form-fitting manner axially and rotationally to a conventional commercial wire at any desired location so that tensile forces or impact forces and/or torques can be transmitted between the wire and the sleeve or another part that is connectable to the sleeve.

In a preferred embodiment, the connecting web is arranged parallel to the longitudinal axis between the front faces on the intermediate ends of the tubular elements, so that there are no parts on the sleeve that protrude beyond the periphery of the tubular elements and could interfere with the removal of the instrument used for fixation of the sleeve.

The connecting web preferably has a cross-sectional area that is orthogonal to the longitudinal axis and is within a circular ring segment with a central angle $\alpha$ between 5° and 350°. The cross-sectional area of the connecting web is of such dimensions that the connecting web can be sheared with a simple instrument that is operable by hand without applying any great force. The fixation of the sleeve to the wire is accomplished by shearing of the connecting web.

In another embodiment, the outer lateral surfaces of the tubular elements each have a planar surface parallel to the longitudinal axis, so that a twist-proof locking can be guaranteed.

In another embodiment, the sleeve is designed with a conical end facing the tip of the wire and has a conical thread. Therefore, this yields the advantages that
   a wire designed with a thread at the tip, for example, may be used as a bone screw together with a sleeve connectable to the bone plate in a stable angle as the screw head; or
   the thread on the sleeve can be screwed directly into a bone or a bone fragment, so that the wire together with the sleeve may be used as a compression screw.

In yet another embodiment, the sleeve is provided with a continuous bore that does not cut through the central bore, so that a wire or thread can be secured on the sleeve and thus on the wire.

In one embodiment of the device, two sleeves are secured at the desired mutual spacing on a wire. The distance between the sleeves in relation to one another is freely selectable. This yields the advantage that two or more bone fragments can be secured between the sleeves. The ends of the sleeve directed toward the bone or the bone fragments may be designed as simple supports or may be provided with a thread.

BRIEF DESCRIPTION OF THE DRAWINGS

The invention and further embodiments of the invention are described in greater detail below on the basis of the partially schematic diagrams of several exemplary embodiments.

FIG. 4 shows a longitudinal section through an embodiment of the inventive device prior to its fixation; and FIG. 5 shows a longitudinal section through the embodiment of the inventive device shown in FIG. 3 in the fixated state.

DETAILED DESCRIPTION OF THE PREFERRED EMBODIMENTS

Figure 1:
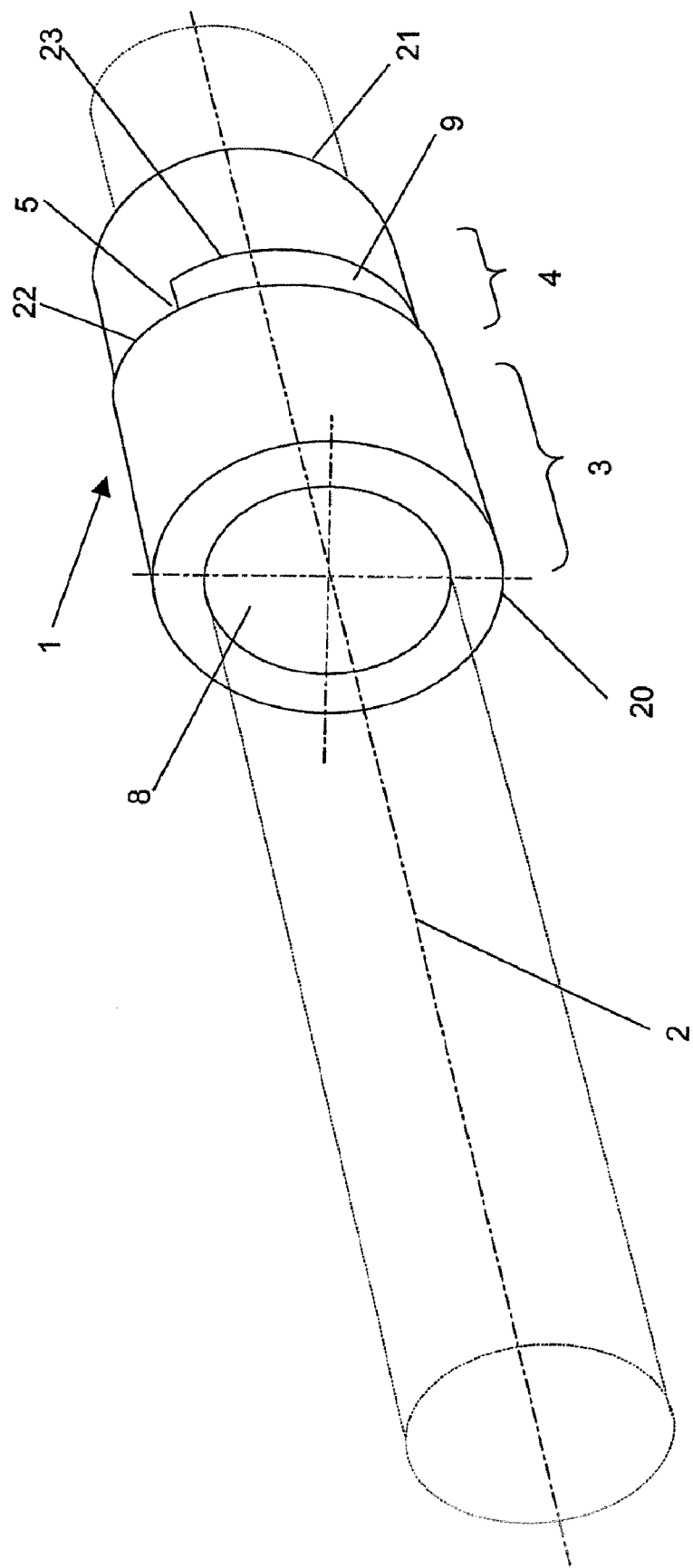
FIG. 1 shows a perspective view of an embodiment of the inventive sleeve.
Figure 2:
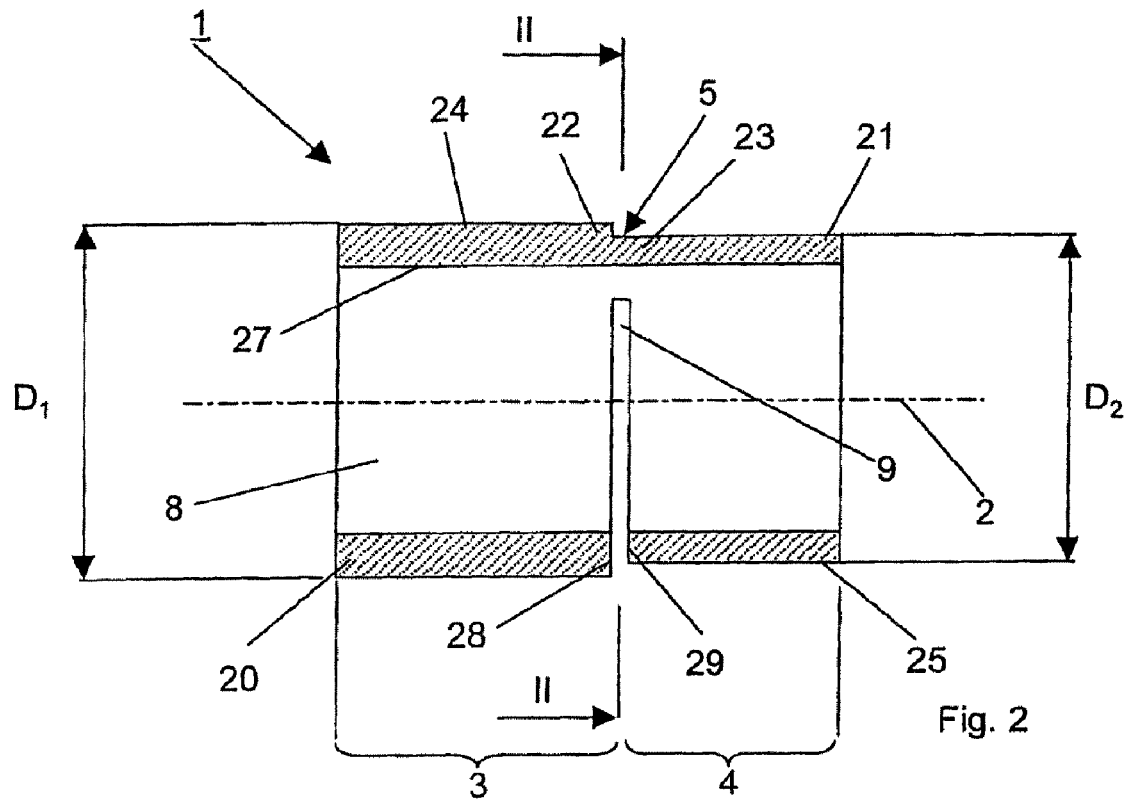
FIG. 2 shows a longitudinal section through the embodiment of the inventive sleeve shown in FIG. 1.
Figure 3:
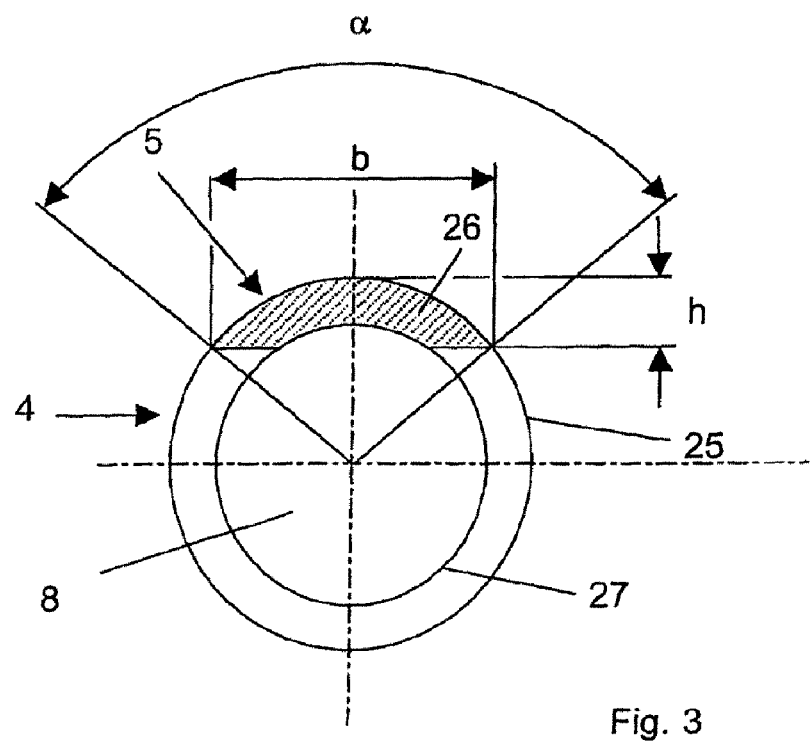
FIG. 3 shows a section along line II-II in FIG. 2.

FIGS. 1 through 3 illustrate an embodiment of a one-piece sleeve having two tubular elements 3; 4 arranged in succession and coaxially with a longitudinal axis 2, said tubular elements being joined together in an axially fixed relationship by means of a connecting web 5. The tubular elements 3; 4 each have an axially protruding end 20; 21, an intermediate end 22; 23 and a coaxial central bore 8. The two tubular elements 3; 4 are also designed as circular cylinders, where the lateral surface 24 of the first tubular element 3 has a diameter $D_1$ and the lateral surface 25 of the second tubular element 4 has a diameter $D_2$. The difference between the diameter $D_1$ of the first tubular element and the diameter $D_2$ of the second tubular element is such that this second tubular element 4 does not protrude radially beyond the first tubular element 3, i.e., $(D_1-D_2)/2 \geqq E$ in the case of shearing of the connecting web 5 across the longitudinal axis 2 by a distance E (FIG. 4). Due to the fact that the second tubular element 4 does not protrude beyond the first tubular element 3 after fixation of the sleeve 1, it is possible to achieve the result that the instrument used for fixation can be removed easily from the sleeve 1.

The sleeve 1 shown here has a radial slot 9 between the intermediate ends 22; 23 of the tubular elements 3; 4, its depth T being smaller than the outside diameter $D_2$ of the second tubular element 4. The connecting web 5 is arranged parallel to the longitudinal axis 2 and on the front faces 28; 29 orthogonal to the longitudinal axis 2 it is fixedly connected to the two tubular elements 3; 4 on the intermediate ends 22; 23.

As shown in FIG. 3, the connecting web 5 is designed as a circular ring segment having a central angle α of approx. 90° in a cross section orthogonal to the longitudinal axis 2, where the inside diameter of the circular ring segment 26 corresponds to the diameter d of the central bore 8 in the tubular elements 3; 4 and the outside diameter of the circular ring segment 26 corresponds to the outside diameter $D_2$ of the second tubular element 4. Due to the fact that the connecting web 5 in the undeformed state borders on the wall 27 of the central bore 8 on the inside (FIG. 3), this yields the result that after shearing of the connecting web 5 across the longitudinal axis 2 (FIG. 5), the connecting web protrudes partially into the central bore 8a in the first tubular element 3 and forms an axial stop for the wire 10, in particular a Kirschner wire. The cross-sectional area q of the connecting web 5 embodied as a circular ring segment 26 must be shearable across the longitudinal axis 2 while also being stable enough to absorb axial forces between the sleeve 1 and the wire 10 (FIG. 5) and to absorb torques between the two tubular elements 3; 4.

The embodiment of the device depicted in FIGS. 4 and 5 comprises a wire having a thread 11 on its distal end 12 and a sleeve 1 which differs from the sleeve 1 depicted in FIGS. 1 through 3 only in that the first tubular element 3 comprises an axial segment 15 having a thread 16. The segment 15 may in particular be implemented as a conical segment having a conical thread 16, whereby the conical thread 16 tapers toward the exterior end 20 of the first tubular element 3. FIG. 4 shows the device prior to fixation, so that the sleeve 1 is axially displaceable on the wire 10. In FIG. 5, the device is depicted with the sleeve 1 secured on the wire 10. Fixation is accomplished by means of an instrument (not shown) by simultaneous shaping, in particular by shearing the wire 10 and the sleeve 1 positioned on it in the area of the connecting web 5 by an amount E, measured across the longitudinal axis 2. Due to the fact that the wire 10 and the connecting web 5 are sheared and the central bores 8a, 8b of the two tubular elements 3; 4 are eccentric relative to one another by the amount E after shearing, this yields an axially and rotationally form-fitting fixation of the sleeve 1 on the wire 10.

The surgical technique during implantation of the inventive device preferably comprises the following steps:
a) screwing a wire into the bone to be treated;
b) applying the sleeve to the wire, in particular a Kirschner wire, optionally by means of a suitable instrument;
c) pushing the instrument onto the sleeve on the wire;
d) correct positioning of the instrument;
e) applying an optimal axial prestress between the wire and the sleeve and thus to the bone fragments to be treated;
f) fixation of the sleeve on the wire;
g) optionally severing the wire on the proximal end of the sleeve; and
h) removing the instrument.

The invention claimed is:

1. A sleeve for attachment to an end of a bone fixation element comprising: first and second tubular elements sharing a common central longitudinal axis, each of the first and second tubular elements having a central bore with a diameter D, an exterior end, and an intermediate end with a front face having a surface area orthogonal to the central longitudinal axis; and a shearable connecting web axially connecting the two tubular elements to one another, wherein the first tubular element and second tubular element are configured and adapted to be axially secured to a bone fixation element inserted within the central bore by partially shearing the connecting web, wherein the partial shearing of the web forms an axial stop at the web within the sleeve.

2. The sleeve of claim 1, wherein the connecting web is parallel to the central longitudinal axis between the front faces on the intermediate ends of the first and second tubular elements.

3. The sleeve of claim 1, wherein the connecting web has a cross-sectional area that is orthogonal to the central longitudinal axis.

4. The sleeve of claim 3, wherein the cross-sectional area of the connecting web is shaped as a circular ring segment having a central angle α between 5° and 350°.

5. The sleeve of claim 1, wherein each of the first and second tubular elements includes an outer lateral surface extending parallel to the central longitudinal axis.

6. The sleeve of claim 1, wherein the second tubular element has a cross-sectional area Q orthogonal to the central longitudinal axis on its intermediate end, and the connecting web has a cross-sectional area q orthogonal to the central longitudinal axis, where the ratio q/Q is between about 0.05 and 0.95.

7. The sleeve of claim 1, wherein the connecting web has a cross sectional area q orthogonal to the central longitudinal axis, where q is between 0.05 $mm^2$ and 40 $mm_2$.

8. The sleeve of claim 1, wherein the connecting web has a cross sectional area q orthogonal to the central longitudinal axis with a width b and a height h, where the ratio h/b is between 0.1 and 1.

9. The sleeve of claim 1, wherein the first and second tubular elements and the connecting web are formed as a single, monolithic unit.

10. The sleeve of claim 1, wherein the first and second tubular elements have first and second outside diameters, and the sleeve further comprises a radial slot between the first and second tubular elements, the slot having a radial depth T less than the outside diameters of the first and second tubular elements.

11. The sleeve according to claim 1, wherein the first and second tubular elements are metallic.

12. The sleeve of claim 11, wherein the first and second tubular elements are formed of steel, steel alloy, titanium, or titanium alloy.

13. The sleeve of claim 1, wherein the first tubular element has an outside diameter $D_1$ and the second tubular element has an outside diameter D, such that $D_2<D_1$.

14. The sleeve of claim 1, wherein the first tubular element includes a threaded portion on its exterior end.

15. The sleeve of claim 14, wherein the threaded portion is conical.

16. The sleeve of claim 1, wherein at least a portion of the connecting web is configured and dimensioned to project into the central bore upon partial shearing of the connecting web.

17. A bone fixation device comprising:
 a longitudinal bone fixation element having at least a first end configured to engage bone and a second end; and
 a sleeve for attachment to the second end of the bone fixation element, the sleeve including first and second tubular elements sharing a common central longitudinal axis, each of the first and second tubular elements having a central bore with a diameter D, an exterior end, and an intermediate end with a front face having a surface area orthogonal to the central longitudinal axis, and a shearable connecting web axially connecting the two tubular elements to one another, wherein the sleeve is axially secured to the bone fixation element by partially shearing the connecting web and the bone fixation element web, wherein the partial shearing forms an axial stop within the sleeve at at least one of the connecting web and the bone fixation web.

18. The device of claim 17, wherein the first tubular element includes a threaded portion on its exterior end.

19. A bone fixation method comprising:
 inserting a longitudinal bone fixation element into a bone, the bone fixation element having at least a first end configured to engage bone and a second end;
 placing a sleeve over the second end of the bone fixation element, the sleeve including first and second tubular elements sharing a common central longitudinal axis, each of the first and second tubular elements having a central bore with a diameter D, an exterior end, and an intermediate end with a front face having a surface area orthogonal to the central longitudinal axis, and a shearable connecting web axially connecting the two tubular elements to one another, and
 partially shearing at least a portion of the connecting web and the bone fixation element to axially secure the sleeve to the bone fixation element by forming an axial stop within the sleeve at at least one of the connecting web and the bone fixation element web.

20. The method of claim 17, further comprising severing at least a portion of the bone fixation element near the second end of the bone fixation element.

\* \* \* \* \*